Figure 1:
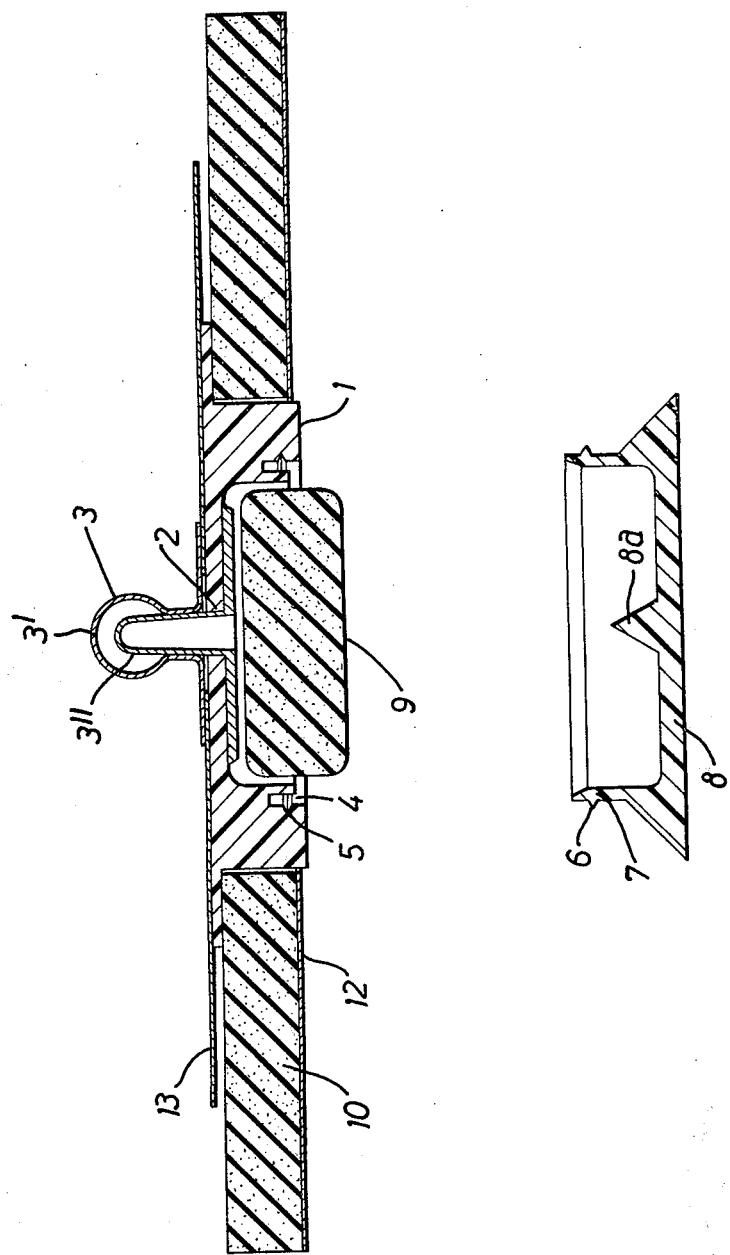

United States Patent [19]
Bowles et al.

[11] 3,942,517
[45] Mar. 9, 1976

[54] ELECTRODES

[75] Inventors: Leslie Reginald Bowles, Dunkirk; Roy Albert Heath-Coleman, Ivy Hatch, both of England

[73] Assignee: Dracard Limited, Maidstone, England

[22] Filed: May 28, 1974

[21] Appl. No.: 473,932

[30] Foreign Application Priority Data
Dec. 3, 1973 United Kingdom............... 55939/73

[52] U.S. Cl........... 128/2.1 E; 128/417; 128/DIG. 4
[51] Int. Cl.²............................................ A61B 5/04
[58] Field of Search ....... 128/2.06 E, 2.1 E, DIG. 4, 128/417, 418, 416, 404, 405; 401/202, 213; 220/306, 307

[56] References Cited
UNITED STATES PATENTS

| | | | |
|---|---|---|---|
| 2,895,479 | 7/1959 | Lloyd | 128/DIG. 4 |
| 3,163,166 | 12/1964 | Brant et al. | 128/405 |
| 3,295,515 | 1/1967 | Kahn | 128/2.06 E |
| 3,610,229 | 10/1971 | Zenkich | 128/2.06 E |
| 3,701,346 | 10/1972 | Patrick et al. | 128/417 |
| 3,713,435 | 1/1973 | Szpur | 128/2.06 E |
| 3,830,229 | 8/1974 | Johnson | 128/2.1 E |

FOREIGN PATENTS OR APPLICATIONS
1,107,745 1/1956 France................................. 220/306

*Primary Examiner*—Robert W. Michell
*Assistant Examiner*—Lee S. Cohen
*Attorney, Agent, or Firm*—Brumbaugh, Graves, Donohue & Raymond

[57] ABSTRACT

A pre-gelled electrode for use on a patient's skin comprises a non-conductive gel-container, a conductive gel within the gel-container, a metal contact having a conductive connection with the gel, a cap which engages with the gel container to hermetically close the gel-container and means for controlling the flow of gel onto the skin after removal of the cap and has an improved shelf-life. The metal contact includes a gelatinous substance to prevent corrosion.

6 Claims, 3 Drawing Figures

U.S. Patent   March 9, 1976   Sheet 2 of 2   3,942,517

ELECTRODES

This invention concerns improved electrodes, especially disposable electrodes suitable for medical use, particularly for monitoring and/or recording the body's electrical impulses.

An object of the invention is to devise an electrode with an extended shelf life of disposable pre-gelled electrodes.

A further object of the invention is the provision of a disposable pre-gelled electrode whose shelf-life does not depend on the packaging thereof.

The invention provides a pre-gelled electrode for use on a patient's skin, which comprises a metal contact, a non-conductive gel-container, a conductive gel within the gel-container, a metal contact in conductive connection with the gel, a cap which engages with the gel-container to hermetically close the gel-container, and means for controlling the flow of gel onto the patient's skin after removal of the cap.

Preferably both the gel-container and the cap are of plastics material. Preferably the cap has a skirt portion with a circumferential lip which engages a corresponding annular groove in the gel-container.

The means for controlling the flow of gel onto the patient's skin may suitably be a foam material, particularly a reticulated plastics foam. Alternatively, the gel-container may comprise a perforated valve plate defining with the gel-container a gel reservoir; in use the gel may ooze through the perforations onto the skin. With the latter form, preferably the cap also comprises a portion which engages the valve plate and seals the perforations.

In its preferred embodiments, the electrode of the present invention gives an essentially hermetic seal to protect the gel, and yields a desirable shelf-life of 12 months or more. Such a shelf-life is attained in the preferred embodiments independent of packaging devices such as foil and plastics film packaging, although the electrodes are preferably protected by such packaging. The electrodes are conveniently sterilised once completely manufactured and this may suitably be done after packaging, by γ- ray radiation.

Figure 2:
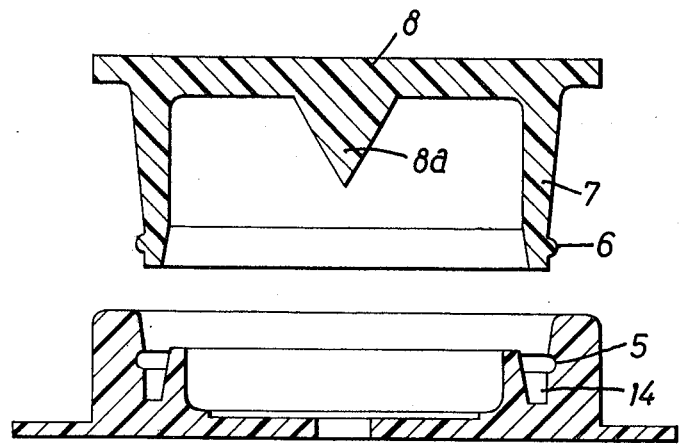
Figure 3:
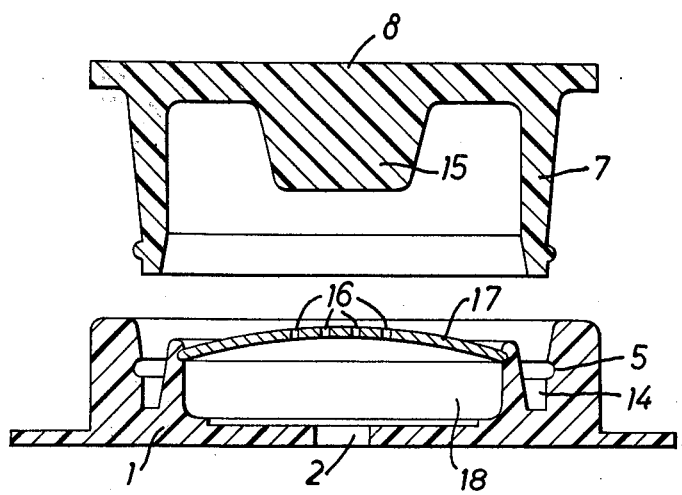

Some preferred embodiments of the invention will now be described hereinafter, with reference to the accompanying drawings, in which:

FIG. 1 is an exploded view in cross-section of a first embodiment of the invention, FIG. 2 is a cross section of a cap and gel-container of the first embodiment of the invention, and FIG. 3 is an exploded view in cross-section of a second embodiment of the invention.

In FIGS. 1 and 2, a circular plastics gel-container 1 suitably of polyethylene has a central hole 2 through which a two-part metal press-stud 3 projects. The contact portion or stud 3' is suitably brass which is nickel plated, and the inner portion or fastener 3" is preferably brass which is silver plated for reasons of electrical conductivity. The fastener 3" is force fitted into the hollow portion of the stud 3'. The press-stud 3 seals the hole 2. The gel-container 1 has an inner annular groove 4,14 with a groove 5, with which a corresponding lip 6 on the skirt portion 7 of a cap 8 mates. The gel-container 1 has within it a loose cylindrical portion of plastics reticulated foam 9, which is impregnated with a conventional compounded gel (not shown) for example a conventional saline gel which is electrically conductive. The cap 8 conveniently has a conical central portion 8a which compresses the foam 9 to decrease the tendency of the foam to drop out of the gel-container 1 when the cap 8 is removed. To attach the electrode to the skin for monitoring and/or recording the body's electrical signals, the electrode has a surrounding foam pad 10 coated with a suitable medical adhesive 12 on the surface to be in contact with the patient's skin. The adhesive layer 12 is suitably covered and protected by a paper sheet which may be stripped off before application of the electrode to the skin. A vinyl sheet or label 13 is adhesively connected to the outer surface of pad 10 and the outer surface of the gel-container 1. A terminal with a lead (not shown) will be attached to the stud 3' to permit the electrode to be connected up to a recording machine, for example.

FIG. 3 illustrates a further construction of gel-container and cap. The cap 8 has an extended central portion 15 which engages and seals the perforations 16 of a valve plate 17 mounted in the gel-container 1. In this construction gel is contained in the space 18 enclosed by gel-container 1 and valve plate 17. On removal of the cap 8, gel may escape through perforations 16 onto the skin of the patient.

It has been discovered that during assembly of the electrodes illustrated, the inner portion or fastener 3" may split or the silver plating which is preferred may split or flake when it is forced into the contact portion or stud 3'. The occurrence of chemical action and other undesirable corrosion may be prevented by the inclusion of a barrier between the gel and the area of metal which comes under attack. As the area is small the barrier should be tenacious and remain in situ throughout the electrode's shelf life and usage. It should not suffer gel attack or deteriorate in any way. A preferred barrier involves the injection of a hardenable material, preferably a plastic gelatinous substance, especially a gelatinous substance dissolved in ether, into the hollow portion of the stud 3' before assembly. This is advantageous in the prevention of corrosion but best results are obtained when the stud 3' and the inner portion or fastener 3" are chemically clean.

What we claim is:

1. A pre-gelled electrode, comprising a resilient non-conductive gel-container having on one side thereof a cavity adapted to open to the skin of a patient, an annular groove surrounding said cavity and adapted to open to the skin of a patient, said annular groove forming an inner wall and an outer wall and having on at least one of said walls another groove, and a central aperture communicating between said cavity and the side of said gel-container opposite said cavity; a conductive gel within said cavity; a metal contact in conductive connection with said gel and passing through said gel-container from said cavity to the side of said gel-container opposite said cavity, said metal contact including a metal fastener projecting from said cavity through said central aperture and a hollow metal stud located on the side of said gel-container opposite said cavity and receiving said metal fastener, wherein said metal fastener and said hollow metal stud seal said central aperture in said gel-container, said hollow metal stud containing chemical means for preventing said gel from contacting that portion of said metal fastener within said hollow metal stud, whereby chemical attack or corrosion of that portion of said metal fastener within said hollow metal stud is prevented; a removable cap covering said cavity, said cap having a skirt portion with a circumferential lip, said skirt portion engaging both said inner wall and said outer wall of said annular groove and said lip engaging said another groove, whereby said cap covers and hermetically seals said cavity to ensure sterility and prevent dehydration of said gel; means adjacent said gel-container for attaching said gel-container to the skin of a patient after the removal of said cap; and means for controlling the flow of said gel onto the skin of a patient after the removal of said cap.

2. An electrode as claimed in claim 1, wherein said gel-container and said cap are made of plastics material.

3. An electrode as claimed in claim 1, wherein said means for controlling the flow of said gel comprises a reticulated plastics foam positioned in said cavity of said gel-container.

4. An electrode as claimed in claim 1, wherein said means for controlling the flow of said gel comprises a perforated valve plate defining with said gel-container a gel reservoir.

5. An electrode as claimed in claim 4, wherein said cap comprises a portion engaging said valve plate and sealing said perforations.

6. An electrode as claimed in claim 1, wherein said chemical means comprises a gelatinous substance.

* * * * *